(12) United States Patent
Ranganathan et al.

(10) Patent No.: US 6,905,986 B2
(45) Date of Patent: Jun. 14, 2005

(54) COMPOSITES COMPRISING SUPERABSORBENT MATERIALS HAVING A BIMODAL PARTICLE SIZE DISTRIBUTION AND METHODS OF MAKING THE SAME

(75) Inventors: Sridhar Ranganathan, Suwanee, GA (US); Richard Norris Dodge, II, Appleton, WI (US); Michael John Niemeyer, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 232 days.

(21) Appl. No.: 09/974,165

(22) Filed: Oct. 9, 2001

(65) Prior Publication Data

US 2003/0129914 A1 Jul. 10, 2003

(51) Int. Cl.[7] .................................................. B32B 5/16
(52) U.S. Cl. ..................................... 442/118; 442/417
(58) Field of Search ................................ 442/118, 153, 442/417

(56) References Cited

U.S. PATENT DOCUMENTS

| | | | |
|---|---|---|---|
| 4,699,823 A | * 10/1987 | Kellenberger et al. ...... 428/219 |
| 4,710,187 A | 12/1987 | Boland et al. | |
| 4,762,521 A | 8/1988 | Roessler et al. | |
| 4,770,656 A | 9/1988 | Proxmire et al. | |
| 4,798,603 A | 1/1989 | Meyer et al. | |
| 5,061,259 A | 10/1991 | Goldman et al. | |
| 5,419,956 A | 5/1995 | Roe | |
| 5,466,513 A | 11/1995 | Wanek et al. | |
| 5,505,718 A | 4/1996 | Roe et al. | |
| 5,601,542 A | 2/1997 | Melius et al. | |
| 5,713,881 A | 2/1998 | Rezai et al. | |
| 5,714,156 A | * 2/1998 | Schmidt et al. ............. 424/404 |
| 5,800,419 A | 9/1998 | Soga et al. | |
| 6,323,388 B1 | * 11/2001 | Melius et al. ............... 604/368 |
| 2003/0098115 A1 | 5/2003 | Dodge, II et al. | |

FOREIGN PATENT DOCUMENTS

| | | |
|---|---|---|
| DE | 198 13 443 A1 | 10/1998 |
| DE | 199 17 919 A1 | 2/2001 |
| EP | 0 781 539 A2 | 7/1997 |
| WO | WO 99/63924 A1 | 12/1999 |
| WO | WO 03/030954 A1 | 4/2003 |

OTHER PUBLICATIONS

Furnas, C.C., Industrial and Engineering Chemistry, vol. 23, No. 9, 1931, pp. 1052–1058.

* cited by examiner

Primary Examiner—Terrel Morris
Assistant Examiner—A B Sperty
(74) Attorney, Agent, or Firm—Ralph H. Dean, Jr.; Bryan R. Rosiejka

(57) ABSTRACT

The present invention is directed to an absorbent composite containing superabsorbent material. The superabsorbent material is in the form of superabsorbent particles having a bimodal particle size distribution. Use of superabsorbent material having a bimodal particle size distribution in the absorbent structure results in enhanced fluid distribution and fluid intake of the absorbent composite. The absorbent composite of the present invention is useful in disposable personal care products.

55 Claims, 2 Drawing Sheets

Particle Size Distribution of AFA 177-9A and 9B at various large:small mass ratios

COMPOSITES COMPRISING SUPERABSORBENT MATERIALS HAVING A BIMODAL PARTICLE SIZE DISTRIBUTION AND METHODS OF MAKING THE SAME

FIELD OF THE INVENTION

The present invention relates to composites containing superabsorbent materials and more particularly to composites containing superabsorbent materials having a bimodal particle size distribution that exhibit improved fluid intake and distribution properties.

BACKGROUND OF THE INVENTION

The use of water-swellable, generally water-insoluble absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products, while reducing their overall bulk. Such absorbent materials are generally present as a composite of superabsorbent particles (SAP) mixed in a fibrous matrix, such as a matrix of wood pulp fluff. A matrix of wood pulp fluff generally has an absorbent capacity of about 6 grams of liquid per gram of fluff. The superabsorbent materials (SAM) generally have an absorbent capacity of at least about 10 grams of liquid per gram of SAM, desirably of at least about 20 grams of liquid per gram of SAM, and often up to about 40 grams of liquid per gram of SAM. Clearly, incorporation of such absorbent materials in personal care products can reduce the overall bulk, while increasing the absorbent capacity of such products.

Capillary driven fluid distribution within the absorbent material is typically hindered due to the presence of the superabsorbent. The fluid distribution may be enhanced by optimizing various superabsorbent physical and functional attributes; however, such modifications traditionally have reduced the pressure driven (forced flow) fluid intake performance of the absorbent core.

Different superabsorbent particle sizes have been used to enhance different composite performance attributes, such as composite intake and distribution. Large particles have been used to create larger voids when swelling to improve fluid intake rate; however, these particles negatively affect fluid distribution. Smaller particles have been used to create smaller voids when swelling to improve capillarity and rate of fluid distribution. However, neither approach has been able to improve one of the properties of intake or distribution without negatively affecting the other property.

What is needed in the art is a composite material comprising superabsorbent material, wherein the composite material has improved intake, as well as, improved distribution.

SUMMARY OF THE INVENTION

The present invention is directed to an absorbent composite including a superabsorbent material (SAM), wherein the superabsorbent material (SAM) contains superabsorbent particles having a bimodal particle size distribution. The bimodal particle size distribution includes large particles having a mass median particle size from about 850 to about 1800 microns, and small particles having a mass median particle size from about 50 to about 200 microns. The bimodal particle size distribution of the superabsorbent particles in the absorbent structure of the present invention enables enhanced capillary driven fluid distribution, as well as improved fluid intake of the absorbent core.

More particularly, the absorbent composite of the present invention contains superabsorbent particles having an overall mass median particle size of about 60 to about 1750 microns. The mass ratio of large particles to small particles is from about 90:10 to about 50:50, and the absorbent composite may comprise from about 20% to about 100% by weight superabsorbent material.

The present invention is also directed to an absorbent composite including a superabsorbent material having a bimodal particle size distribution, wherein the composite has a third liquid insult intake time of less than about 100 seconds.

The present invention is further related to an absorbent composite containing superabsorbent material which is uniformly distributed within the composite. The composite has a third liquid insult intake time of less than about 100 seconds, and a third intermittent vertical wicking pickup time of less than about 600 seconds.

The absorbent composite is particularly useful in disposable personal care products such as diapers, training pants, feminine pads, panty liners, incontinence products, as well as personal health products such as wound dressings, and delivery systems.

DETAILED DESCRIPTION OF THE INVENTION

At the levels of SAM currently used in the absorbent core of diapers (about 40%), the volume occupied by the superabsorbent material (SAM) as it swells becomes significantly greater than that occupied by the fibrous material. Though the fibers continue to play an important role in capillary driven fluid movement on subsequent fluid insults, adjusting the packing fraction of the swollen superabsorbent particles to maximize the capillary drive can lead to significantly improved fluid wicking. As used herein, the term "packing fraction" refers to the ratio of solid volume to total volume of the composite.

The present invention fulfills the above-described need by providing an absorbent composite having enhanced fluid intake of the absorbent core and improved capillary driven fluid distribution. Uniform distribution of the superabsorbent material within the absorbent composite is preferred. In one embodiment of the present invention, the improved properties of the absorbent composites of the present invention result from the use of a SAM having a bimodal distribution of superabsorbent particle sizes within the absorbent core.

The following terms are used to describe the absorbent composites of the present invention. A general definition of each term is given below.

Figure 1:
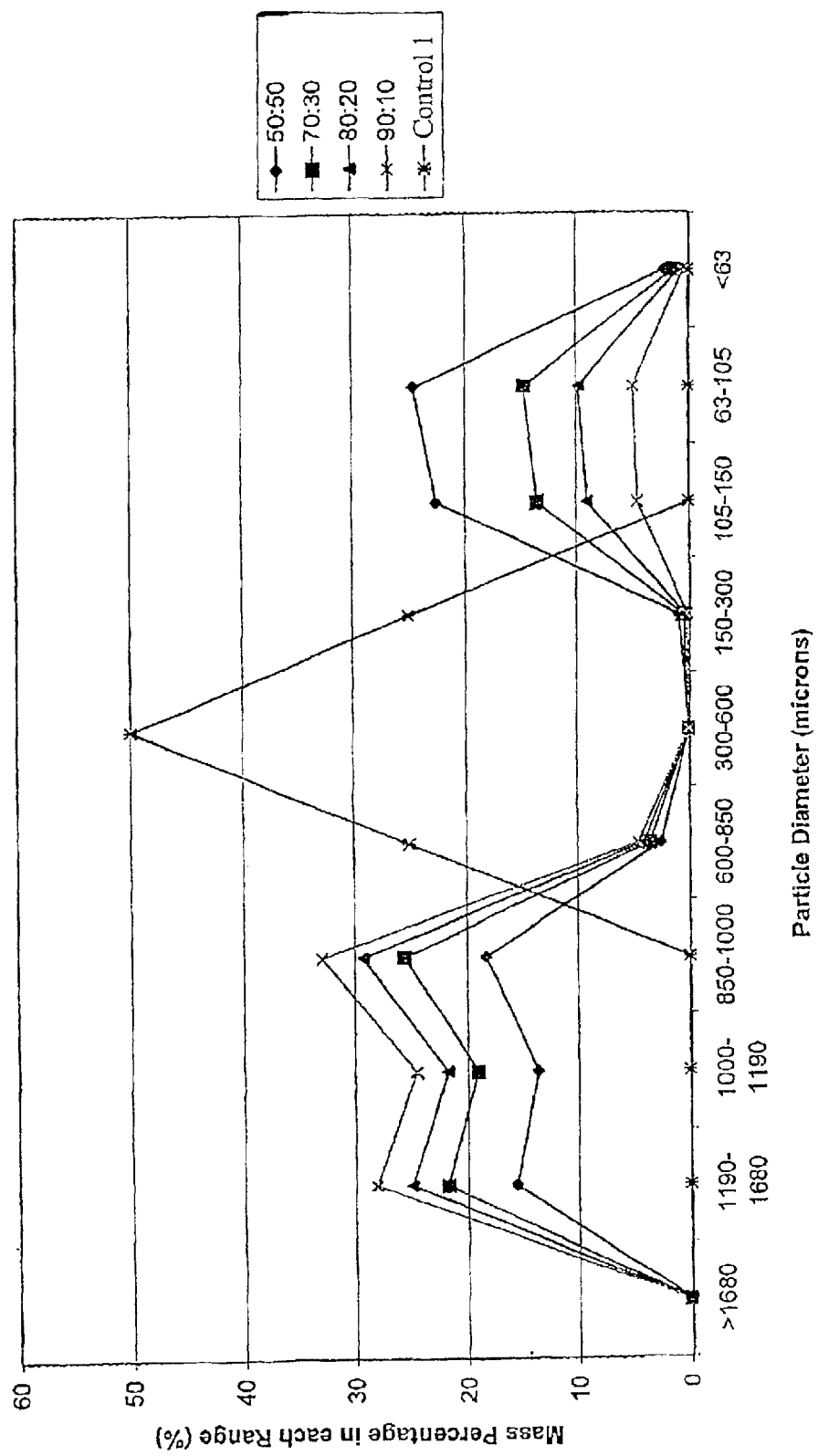
FIG. 1 is a graph illustrating the relationship of mass fraction versus particle size for superabsorbent materials used in the present invention.

As used herein, the term "bimodal" refers to a superabsorbent material having two distinct peaks in the mass fraction versus particle size curve for the superabsorbent material. A graph containing the mass fraction versus particle size curves for several SAMs is illustrated in FIG. 1.

As used herein, the term "superabsorbent material" refers to a water-swellable, water-insoluble organic or inorganic material capable, under the most favorable conditions, of absorbing more than 15 times its weight in an aqueous solution containing 0.9 weight percent sodium chloride.

As used herein, the term "uniform distribution" with respect to superabsorbent material means the absorbent composite has an equal amount of superabsorbent material located in all three dimensions of the composite.

Desirably, the absorbent composites of the present invention comprise superabsorbent material in combination with a fibrous matrix containing one or more types of fibrous materials. A discussion of the absorbent composite components is given below.

Superabsorbent Materials

Materials suitable for use as a superabsorbent material of the present invention may include natural materials such as agar, pectin, guar gum, and the like; as well as synthetic materials, such as synthetic hydrogel polymers. Such hydrogel polymers include, but are not limited to, alkali metal salts of polyacrylic acids, polyacrylamides, polyvinyl alcohol, ethylene maleic anhydride copolymers, polyvinyl ethers, hydroxypropylcellulose, polyvinylmorpholinone; and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride copolymers and mixtures thereof. The hydrogel polymers are desirably lightly crosslinked to render the material substantially water insoluble. Crosslinking may, for example, be by irradiation or by covalent, ionic, van der Waals, or hydrogen bonding. The superabsorbent materials may be in any form suitable for use in absorbent composites including particles, flakes, spheres, and the like.

While a wide variety of superabsorbent materials are known, the present invention relates, in one aspect, to the proper selection of superabsorbent materials to allow the formation of improved absorbent composites and disposable absorbent garments. The present invention is directed to a method of achieving optimum performance in an absorbent composite due to the discovery that superabsorbent materials having a particular bimodal particle size distribution provide unexpected improvements in the combined properties of capillary driven fluid distribution and intake performance. More specifically, the absorbent composites of the present invention desirably contain superabsorbent material having a bimodal particle size distribution, wherein the superabsorbent material comprises large particles having a mass median particle size of from about 850 to about 1800 microns and small particles having a mass median particle size of from about 50 to about 200 microns. Preferably, the superabsorbent material contains large particles having a mass median particle size from about 1000 to about 1600 microns and small particles having a mass median particle size from about 65 to about 150 microns.

Another desirable feature of the present invention is the difference between the mass median particle size of the large particles and the mass median particle size of the small particles within the absorbent composites of the present invention. Desirably, the ratio of the mass median particle size of the large particles to the mass median particle size of the small particles is from about 4:1 to about 36:1. More desirably the ratio of the mass median particle size of the large particles to the mass median size of the small particles is from about 6:1 to about 25:1.

In one embodiment of the present invention, the absorbent composite contains superabsorbent material having a bimodal particle size distribution, wherein the superabsorbent material includes large particles having a mass median particle size of less than about 1200 microns, and small particles having a mass median particle size of less than about 150 microns, wherein the difference ($d_{l/s}$) between the mass median particle size of the large particles and the mass median particle size of the small particles is greater than about 500 microns. In a further embodiment, the absorbent composite contains superabsorbent material having a bimodal particle size distribution, wherein the superabsorbent material includes large particles having a mass median particle size of less than about 1100 microns, and small particles having a mass median particle size of less than about 100 microns, wherein the difference ($d_{l/s}$) between the mass median particle size of the large particles and the mass median particle size of the small particles is greater than about 900 microns.

While not being bound by any particular theory, it is believed that the composites of the present invention exhibit enhanced fluid distribution for the following reasons. In composites containing high levels of superabsorbent material (i.e., greater than 30 wt %), the volume occupied by the superabsorbent material, as it swells, becomes significantly greater than that occupied by the fibers. If there is too much empty space between the particles and fibers (void space), the capillarity of the composite system becomes too low to effectively wick fluid to higher areas in the composite. However, if the packing of the swollen superabsorbent particles can be adjusted to minimize the amount of void space between the swollen superabsorbent particles, the capillary drive within the system will be maintained resulting in improved fluid wicking. Surprisingly, it has been found that composites of the present invention that exhibit improved fluid wicking also exhibit improved fluid intake.

Thus, it is preferred that the superabsorbent material be uniformly distributed within the absorbent composite. However, the superabsorbent material may be distributed throughout the entire absorbent composite or may be distributed within a small, localized area of the absorbent composite.

Relationships have been identified between the amount of void space in multi-component systems and the ratio of the smallest and largest particles in the system. From these relationships, the maximum packing of particles in a two-component system can be determined. See C. C. Furnis, *Industrial and Engineering Chemistry*, vol. 23, no. 9, 1052–1058 (1931). The equation that is used is:

$$\Phi = \phi_1 + (1-\phi_1)$$

$$\phi_1 = [(1-v_1) \cdot \rho_1] + [(1-v_1) \cdot \rho_1 + v_1 \cdot (1-v_2) \cdot \rho_2]$$

wherein $v_1$ and $v_2$ are the void space in a system of particles 1 (i.e., the large particles) and particles 2 (i.e., the small particles), respectively; and $\rho_1$ and $\rho_2$ are the true specific gravity of particles 1 (i.e., the large particles) and particles 2 (i.e., the small particles), respectively. The value of $\phi_1$ represents the degree to which the first component, the large particles, is saturated by the second component, the small particles. The weight of the large particles for densest packing will be $\phi_1$ and the weight of the small particles for densest packing will be $(1-\phi_1)$.

Each of these quantities divided by $\Phi$ will then give the proportion, by weight, of each component for densest packing. The optimal large particle to small particle ratio can be calculated based on the maximum packing of the particles at full saturation, since, at this saturation level, the packing within the structure will primarily be determined by the superabsorbent material rather than the fibers.

Given the above-described calculation, it has been determined that the absorbent composites of the present invention desirably contain superabsorbent material, wherein the mass ratio of "large" particles (i.e., the sample of particles having the greater mass median particle size) to "small" particles (i.e., the sample of particles having the smaller mass median particle size) is from about 90:10 to about 50:50. More desirably, the absorbent composites of the present invention contain superabsorbent material, wherein the mass ratio of "large" particles to "small" particles is from about 90:10 to about 80:20. Even more desirably, the absorbent composites of the present invention contain superabsorbent material, wherein the mass ratio of "large" particles to "small" particles is about 85:15.

Further, the absorbent composites of the present invention desirably contain the above-described bimodal particle size distribution and an overall mass median particle size of from about 60 to about 1750 microns. More desirably, the absorbent composites of the present invention desirably contain the above-described bimodal particle size distribution and an overall mass median particle size of from about 800 to about 1200 microns. Even more desirably, the absorbent composites of the present invention desirably contain the above-described bimodal particle size distribution and an overall mass median particle size of from about 900 to about 1100 microns.

In one embodiment of the present invention, the superabsorbent material comprises a sodium salt of a cross-linked polyacrylic acid. Suitable superabsorbent materials include, but are not limited to, Dow AFA-177-140 and Drytech 2035 both available from Dow Chemical Company, Midland, Mich., Favor SXM-880 available from Stockhausen, Inc. of Greensboro, N.C., Sanwet IM-632 available from Tomen America of New York, N.Y., and Hysorb P-7050 available from BASF Corporation, Portsmouth, Va.

Fibrous Materials

Desirably, the absorbent composites of the present invention contain the above-described superabsorbent materials in combination with a fibrous matrix containing one or more types of fibrous materials. The fibrous material forming the absorbent composites of the present invention may be selected from a variety of materials including natural fibers, synthetic fibers, and combinations thereof. A number of suitable fiber types are disclosed in U.S. Pat. No. 5,601,542, assigned to Kimberly-Clark Worldwide, Inc., the entirety of which is incorporated herein by reference.

The choice of fibers depends upon, for example, the intended end use of the finished absorbent composite. For instance, suitable fibrous materials may include, but are not limited to, natural fibers such as non-woody fibers, including cotton fibers and cotton derivatives, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, aspen, or the like. Wood fibers may be prepared in high-yield or low-yield forms and may be pulped in any known method, and include kraft, sulfite, groundwood, thermomechanical pulp (TMP), chemithermomechanical pulp (CTMP) and bleached chemithermomechanical pulp (BCTMP). Recycled fibers are also included within the scope of the present invention. Any known pulping and bleaching methods may be used.

Similarly, regenerated cellulosic fibers such as viscose rayon and cuprammonium rayon, modified cellulosic fibers, such as cellulose acetate, or synthetic fibers such as those derived from polyesters, polyamides, polyacrylics, etc., alone or in combination with one another, may likewise be used. Chemically treated natural cellulosic fibers may be used such as mercerized pulps, chemically stiffened or crosslinked fibers, sulfonated fibers, and the like. Suitable papermaking fibers may also include recycled fibers, virgin fibers, or mixtures thereof. Blends of one or more of the above-mentioned fibers may also be used if so desired.

Absorbent Composites

As described above, the absorbent structures according to the present invention desirably include a superabsorbent material and a fibrous matrix for containing the superabsorbent material. However, it should be noted that any device capable of containing the above-described superabsorbent material, and in some cases, is capable of being located in a disposable absorbent garment, is suitable for use in the present invention.

Many such containment devices are known to those skilled in the art. For example, the containment device may comprise a fibrous matrix such as an air-formed or wet-laid web of cellulosic fibers, a meltblown web of synthetic polymeric fibers, a spunbonded web of synthetic polymeric fibers, a coformed matrix comprising cellulosic fibers and fibers formed from the synthetic polymer material, airlaid, heat-fused webs of synthetic polymeric materials, open-celled foams, and the like.

The containment device is desirably a fibrous matrix having a form such as a fibrous network, which is, generally, a random plurality of fibers that can, optionally, be joined together with a binder. The fibrous material can alternatively have the form of a batt of comminuted wood pulp fluff, a tissue layer, a hydroentangled pulp sheet, a woven sheet, a nonwoven sheet, a tow, or a mechanically softened pulp sheet. Any papermaking fibers, as previously defined, or mixtures thereof may be used to form the fibrous matrix.

The absorbent composites of the present invention may be formed from a single layer of absorbent material or multiple layers of absorbent material. In the case of multiple layers, the layers may be positioned in a side-by-side or surface-to-surface relationship and all or a portion of the layers may be bound to adjacent layers. In those instances where the absorbent composite includes multiple layers, the entire thickness of the absorbent composite may contain one or more superabsorbent materials or each individual layer may separately contain some or no superabsorbent materials.

In one embodiment of the present invention, the absorbent composite contains superabsorbent material and fibrous material wherein the relative amount of superabsorbent material and fibrous material used to produce the absorbent composite may vary depending on the desired properties of the resulting product, and the application of the resulting product. Desirably, the amount of superabsorbent material in the absorbent composite is from about 20 wt % to about 100 wt % and the amount of fibrous material is from about 80 wt % to about 0 wt %, based on the total weight of the absorbent composite. More desirably, the amount of superabsorbent material in the absorbent composite is from about 30 wt % to about 90 wt % and the amount of fibrous material is from about 70 wt % to about 10 wt %, based on the total weight of the absorbent composite. Even more desirably, the amount of superabsorbent material in the absorbent composite is from about 40 wt % to about 80 wt % and the amount of fibrous material is from about 60 wt % to about 20 wt %, based on the total weight of the absorbent composite.

In another embodiment, the basis weight of superabsorbent material used to produce the absorbent composites of the present invention may vary depending on the desired properties, such as total composite thickness and basis weight, in the resulting product, and the application of the resulting product. For example, absorbent composites for use in infant diapers may have a lower basis weight and thickness compared to an absorbent composite for an incontinence device. Desirably, the basis weight of superabsorbent material in the absorbent composite is greater than about 80 grams per square meter (gsm). More desirably, the basis weight of superabsorbent material in the absorbent composite is from about 80 gsm to about 800 gsm. Even more desirably, the basis weight of superabsorbent material in the absorbent composite is from about 120 gsm to about 700 gsm. Even more desirably, the basis weight of superabsorbent material in the absorbent composite is from about 150 gsm to about 600 gsm.

Method of Making the Absorbent Composite

The absorbent composites of the present invention may be made by any process known to those having ordinary skill in the art. In one embodiment of the present invention, the method of forming the absorbent composite may include combining superabsorbent material containing superabsorbent particles with a substrate. The superabsorbent particles have a bimodal particle size distribution with large particles having a mass median particle size from about 850 to about 1800 microns and small particles having a mass median size from about 50 to about 200 microns. Preferably, the large particles have a mass median size from about 1000 to about 1600 microns, and the small particles have a mass median size from about 65 to about 150 microns.

Alternatively, the method may include combining superabsorbent material with a substrate wherein the composite has a third liquid insult intake time less than about 100 seconds and a third intermittent vertical wicking pickup time less than about 600 seconds. The superabsorbent material is uniformly distributed within the composite.

In a further embodiment of the present invention, superabsorbent material containing superabsorbent particles is incorporated into an existing substrate. Preferably, the substrate contains fibrous material. Suitable fibrous substrates include, but are not limited to, nonwoven and woven fabrics. In many embodiments, particularly personal care products, preferred substrates are nonwoven fabrics. As used herein, the term "nonwoven fabric" refers to a fabric that has a structure of individual fibers or filaments randomly arranged in a mat-like fashion. Nonwoven fabrics may be made from a variety of processes including, but not limited to, air-laid processes, wet-laid processes, hydroentangling processes, staple fiber carding and bonding, and solution spinning. The superabsorbent material may be incorporated into the fibrous substrate as a solid particulate material. The superabsorbent materials may be in any form suitable for use in absorbent composites including particles, flakes, spheres, and the like.

In an alternative embodiment of the present invention, fibrous material and the superabsorbent material containing superabsorbent particles are simultaneously mixed to form an absorbent composite. Desirably, the composite materials are mixed by an air-forming process known to those of ordinary skill in the art. Air-forming the mixture of fibers and superabsorbent material is intended to encompass both the situation wherein preformed fibers are air-laid with the superabsorbent material, as well as, the situation in which the superabsorbent material is mixed with the fibers as the fibers are being formed, such as through a meltblowing process.

For example, the following description is meant to be illustrative of an air-forming process used to form the composites of the present invention, but is not meant to be limiting. Several process components may be used to make the absorbent composites of the present invention. These include first a method to fiberize pulp sheets into fiberized fluff. These fiberized fluff fibers are conveyed by air into a forming chamber. Next, a method of adding superabsorbent particles is used to meter and convey superabsorbent particles to the forming chamber. More than one superabsorbent feeder has been found to be useful in controlling the individual amounts of superabsorbent particles of different types to the forming chamber. The forming chamber causes the fiberized fluff fibers and the superabsorbent particles to become mixed together. A moving forming screen is located at the bottom of the forming chamber. This screen is air permeable and is typically connected to a vacuum source. This vacuum removes air from the forming chamber and causes the fiberized fluff fibers and superabsorbent particles to be deposited onto the forming screen to form a composite web. Tissue may be unwound onto the forming wire such that the fibers and particles are laid onto the tissue to aid in conveying. The speed of the pulp sheets, superabsorbent feeders, and the forming screen can all be independently adjusted to control the composition and basis weight of the resulting composite. Following formation of the composite web on the forming wire, a roller may be used to compress the composite to a desired level. At the end of the forming screen the composite web is wound into a continuous roll.

Properties of the Absorbent Composites

The absorbent composites of the present invention possess improved capillary driven fluid distribution, as well as, enhanced fluid intake over the life of the composite, when compared to known absorbent composites. One method of measuring the capillary driven fluid distribution of an absorbent composite is with the Intermittent Vertical Wicking (IVW) test. This test measures the rate of wicking of a material or composite during a series of liquid contacts.

The IVW test consists of contacting a lower edge of a vertically suspended absorbent composite with a solution, and is described in detail below. The fluid distribution profile obtained from the IVW test may be analyzed in terms of liquid saturation of the composite at varying distances from the lower edge of the composite. Preferably, the absorbent composites of the present invention display a liquid saturation at 3 to 3.5 inches from the lower edge of the composite equal to at least 65% of the liquid saturation at 0 to 0.5 inches from the lower edge of the composite. More preferably, the liquid saturation at 4 to 4.5 inches from the lower edge of the absorbent composite is equal to at least 50% of the liquid saturation at 0 to 0.5 inches from the lower edge of the composite, and still more preferably the liquid saturation at 4.5 to 5.0 inches from the lower edge of the composite is equal to at least 35% of the liquid saturation at 0 to 0.5 inches from the lower edge of the absorbent composite.

Further, it is desired that the absorbent composites of the present invention demonstrate a third intermittent vertical wicking pickup time of less than about 600 seconds. More desirably, the absorbent composites demonstrate a third intermittent vertical wicking pickup time of less than about 300 seconds.

One method of measuring the fluid intake of an absorbent composite is with the Fluid Intake Evaluation (FIE) test, which is described in detail below. This test measures the intake capability of a material or composite when subjected to multiple liquid insults.

Desirably, an absorbent composite of the present invention possesses a third liquid insult intake time of less than about 100 seconds, more desirably less than about 85 seconds, and even more desirably less than about 60 seconds.

Another unique characteristic of the absorbent composites of the present invention is that the superabsorbent particles contained in the composite have different swelling times due to the distinct sizes of the particles. The swelling time is defined as the amount of time it takes for the superabsorbent particles to reach 60% liquid capacity, and may be determined using the Blotted FAUZL Test which is explained in detail below. Preferably, the swelling time of the small particles used in the absorbent composite of the present invention is from about 15 seconds to about 35 seconds, and the swelling time of the large particles is from about 300 seconds to about 700 seconds. More preferably, the swelling time of the small particles is from about 20 seconds to about 30 seconds, and the swelling time of the large particles is from about 400 seconds to about 600 seconds. In addition, it is desired that the swelling time of the small particles is approximately 20 times shorter than the swelling time of the large particles.

Methods of Using the Absorbent Structures

In one embodiment of the present invention, a disposable absorbent product is provided, which includes a liquid-permeable topsheet, a backsheet attached to the topsheet, and an absorbent composite of the present invention positioned between the topsheet and the backsheet. Those skilled in the art will recognize materials suitable for use as a topsheet and a backsheet. Exemplary materials suitable for use as a topsheet are liquid-permeable materials, such as spunbonded polypropylene or polyethylene having a basis weight of from about 15 to about 25 grams per square meter. Exemplary materials suitable for use as a backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time. The absorbent products of the present invention should be present in an amount effective to form a superabsorbent composition effective to result in the absorption of a desired amount of liquid.

The absorbent composites according to the present invention are suited to absorb many fluids including body fluids such as urine, menses, and blood, and are particularly suited for use in disposable absorbent products such as disposable personal care products including, but not limited to absorbent garments such as diapers, incontinence products, bed pads, and the like; catamenial devices such as sanitary napkins, panty liners, tampons, and the like; personal health products such as wound dressings, and delivery systems; as well as wipes, bibs, food packaging and the like. Accordingly, in another aspect, the present invention relates to a disposable absorbent garment comprising an absorbent composite as described above. A wide variety of absorbent garments are known to those skilled in the art. The absorbent composites of the present invention can be incorporated into such known absorbent garments. Exemplary absorbent garments are generally described in U.S. Pat. No. 4,710,187 issued Dec. 1, 1987, to Boland et al.; U.S. Pat. No. 4,762,521 issued Aug. 9, 1988, to Roessler et al.; U.S. Pat. No. 4,770,656 issued Sep. 13, 1988, to Proxmire et al.; U.S. Pat. No. 4,798,603 issued Jan. 17, 1989; to Meyer et al.; which references are incorporated herein by reference.

As a general rule, the absorbent disposable garments according to the present invention comprise a body-side liner adapted to contact the skin of a wearer, an outer cover superposed in facing relation with the liner, and an absorbent composite, such as those described above, superposed on said outer cover and located between the body-side liner and the outer cover.

TEST METHODS

For Testing Superabsorbent Materials

The methods for determining the particle size distribution and the mass median particle size of a given sample of superabsorbent material is described below. In addition, the method for determining the swelling time and gel bed void space of the superabsorbent particles is set forth below.

Particle Size Distribution (PSD) Test Method

The PSD test method used in the present invention determines the particle size distribution of a superabsorbent material by sieve size analysis. A stack of sieves are used to determine the particle size distribution of a given sample. Thus, for example, in principle, a particle that is retained on a sieve with 710 micron openings is considered to have a particle size greater than 710 microns. A particle that passes through a sieve having 710 micron openings and is retained on a sieve having 500 micron openings is considered to have a particle size between 500 and 710 microns. Further, a particle that passes through a sieve having 500 micron openings is considered to have a particle size less than 500 microns.

The sieves are placed in order of the size of the openings with the largest openings on the top of the stack and the smallest openings on the bottom of the stack. A 25 gram sample of superabsorbent particles is placed into the sieve with the largest openings. The sieve stack is shook for 10 minutes with a Ro-Tap mechanical Sieve Shaker, Model B available from W. S. Tyler of Mentor, Ohio, or other similar shaking device. After shaking is complete, the superabsorbent particles retained on each sieve are removed and the weight is measured and recorded. The percentage of particles retained on each sieve is calculated by dividing the weights of the particles retained on each sieve by the initial sample weight.

Mass Median Particle Size Test Method

As used herein, the term "mass median particle size" of a given sample of superabsorbent particles is defined as the particle size, which divides the sample in half on a mass basis, i.e., half of the sample by weight has a particle size greater than the mass median particle size and half of the sample by mass has a particle size less than the mass median particle size. Thus, for example, the mass median particle size of a sample of superabsorbent particles is 500 microns if one half of the sample by weight is retained on a sieve with openings of 500 microns.

Blotted FAUZL (Flooded Absorbency Under Zero Load) Test

The mass of an Absorbency Under Load (AUL) cup and plunger is weighed and recorded as "Me". The AUL cup is made from one inch inside diameter thermoplastic tubing which is machined-out slightly to obtain concentricity. The AUL cup has a 400 mesh stainless steel screen that is adhered to the bottom of the cup by means of an adhesive. Alternatively, the screen can be fused to the bottom of the cylinder by heating the wire screen in a flame until red hot, after which the AUL cup is held onto the screen until cooled. A soldering iron can be used to touch up the seal if unsuccessful or if it breaks. Care must be taken to maintain a flat, smooth bottom, and not distort the inside of the AUL cup. The plunger is made from one inch diameter solid material (e.g. Plexiglass) and is machined to closely fit without binding in the AUL cup. Prior to placing the superabsorbent onto the screen of the AUL cup, the superabsorbent material is sieved to the appropriate size for testing.

Approximately 0.160 gram of superabsorbent material is placed in the AUL cup, wherein the superabsorbent material is evenly distributed over the bottom of the cup. A plunger weighing 4.0 grams is placed on top of the dry superabsorbent material, thereby yielding a pressure of approximately 0.01 psi. The mass of the AUL cup, plunger and dry superabsorbent material is weighed and recorded as "Mo". 0.9% by weight saline solution is added to a petri dish (at least 2 inches in diameter) to a depth of about 0.5 cm. A plastic screen having approximately 16 openings per square inch is placed on the bottom of the petri dish.

The AUL cup is placed in the saline for 15 seconds to allow the saline to be absorbed into the superabsorbent material. The bottom of the AUL cup is quickly placed on a paper towel to remove any liquid in the screen or in the interstitial spaces between the superabsorbent particles. The time from removal of the AUL cup from the saline to placement on the paper towel should be 3 seconds or less. The cup is moved to dry portions of the paper towel until no more liquid is seen being transferred from the cup to the towel. Next, the AUL cup, plunger and superabsorbent material are weighed and the mass is recorded as "Mt". The total time to remove liquid from the interstitial spaces, weigh the AUL cup, and place the AUL cup back into the saline should be less than 30 seconds. The AUL cup is quickly placed back into the saline for an additional 15 seconds to allow saline to be absorbed by the superabsorbent material. Again, the bottom of the cup is dried and Mt is determined. Mt is obtained for the following cumulative exposure times, wherein "exposure time" is defined as the time the superabsorbent is immersed in the liquid: 0.25, 0.5, 0.75, 1.0, 1.5, 2.0, 2.5, 3.0, 4.0, 5.0, 10, 20, 40 and 60 minutes. The entire test is conducted three times for each superabsorbent material to be examined, and the average pickup for the three replicates is determined for each exposure time.

Data Analysis

The amount of saline picked up during each exposure time is determined by the following equation:

$$g \text{ saline}/g \text{ superabsorbent} = (Mt-Mo)/(Mo-Me)$$

The g/g pickup value at 60 minutes cumulative exposure time is determined and recorded as g/g(e). The characteristic time to reach 60 percent of the 60 minute g/g pickup value is determined by the following equation:

$$\text{Characteristic pickup value} = 0.6 * g/g(e)$$

A table listing the exposure time and pickup value is used to interpolate the characteristic time to pick up 60% of the 60 minute pickup value.

Gel Bed Void Space Experimental Procedure

The Centrifuge Retention Capacity (CRC) of the superabsorbent particles is measured to obtain the full saturation capacity of the gel particles. 2.0 grams of the dry superabsorbent particles is then measured. An amount equal to $(2.0 \times CRC)$ grams of 0.9 wt. % saline solution is measured into a 200 ml beaker. The 2.0 grams of dry superabsorbent particles is added to the 0.9 wt. % saline solution and stirred for 10 seconds to ensure no particle clumping. The beaker is then covered with paraffin or another suitable cover and the superabsorbent is allowed to swell, undisturbed for at least two hours in order for the swelling to reach equilibrium. After the superabsorbent swelling reaches equilibrium, the average swelling height is marked within the beaker by placing a light-weight acrylic platen (<0.02 psi) on top of the swollen gel bed and marking the height of the bottom of the platen on the side of the beaker. The contents of the beaker is then emptied. After the beaker is tared it is filled with water up to the mark designating the height of the swollen gel bed. The beaker is weighed to obtain the total volume of the swollen gel bed using the following equation: Volume= weight (grams)/1.0 gm/cc. The void spaces are then determined by subtracting the volume due to the saline and gel with the formula: Voids=Water Volume$-[((2.0 \times CRC)/(\text{specific gravity of } 0.9 \text{ wt. } \% \text{ saline})) + (2.0 \text{ gm of superabsorbent}/1.5 \text{ gm/cc})]$.

For Testing Absorbent Composites

The test methods for determining the Saturation Capacity (SC), Intermittent Vertical Wicking (IVW), and Fluid Intake Evaluation (FIE) of a given absorbent composite are described below.

Saturation Capacity (SC) Test

A composite of superabsorbent and fluff, or fluff only, is air-formed on tissue to a desired basis weight and density. Composite samples are cut to a desired size, in this case, the composite samples are cut to a 3.5 inch (8.89 cm) by 10 inch (25.40 cm) rectangle. The weight of each composite sample is then measured and recorded. This is the dry weight of the composite. The composite samples are then soaked in a bath of 0.9 wt % NaCl solution for 20 minutes. After 20 minutes of soaking, the composite samples are placed under 0.5 psi (14" $H_2O$) vacuum pressure for 5 minutes. The composite samples are then weighed again. This is the wet composite weight. The capacity of each composite sample is calculated by subtracting the dry composite weight from the wet composite weight for each sample.

Intermittent Vertical Wicking (IVW) Test

The Intermittent Vertical Wicking (IVW) test measures the rate of wicking and the fluid distribution profile of a material or composite during a series of liquid contacts. The test consists of three separate contacts between a lower edge of a vertically suspended absorbent composite sample and a saline solution. Each separate contact, or liquid insult to the composite, represents 15% of the saturation capacity of the absorbent composite as measured in the SC test described above. Each separate liquid insult in the IVW test equals $(0.15) \times (m_{total})$ so that the composite has a desired degree of absorption capacity during each insult. The absorbent composite sample is allowed to wick liquid as described below.

A composite of superabsorbent and fluff, is air-formed on tissue to a desired basis weight and density. Composite samples are cut to a desired size, in this case, the composite samples are cut to a 3.5 inch (8.89 cm) by 10 inch (25.40 cm) rectangle. The saturation capacity of the sample ($m_{total}$) is determined as described above. An amount equal to $(0.15) \times (m_{total})$ is calculated.

A separate sample is vertically suspended so that the long dimension of the sample is in the vertical direction. The suspended sample is attached to a strain gauge. The sample is then lowered into a reservoir containing a 0.9 wt % NaCl solution. The amount of sample which is in contact with the solution should be ¼ inch or less. The amount of liquid pickup is measured as a function of time, and allowed to continue until 15% of the saturation capacity of this absorbent composite $[(0.15) \times (m_{total})]$ has been recorded on the strain gauge. The sample is then removed from the NaCl solution, but is kept in a vertical configuration.

After a period of 30 minutes, the sample is again lowered into the 0.9 wt % NaCl solution. The amount of liquid pickup is measured as a function of time, and allowed to continue until 15% of the saturation capacity of this absorbent composite [$(0.15) \times (m_{total})$] has been recorded on the strain gauge. The sample is then removed from the NaCl solution, but is kept in a vertical configuration.

After a period of 30 minutes, the sample is lowered into the 0.9 wt % NaCl solution for a third time. The amount of liquid pickup is measured as a function of time, and allowed to continue until 15% of the saturation capacity of this absorbent composite [$(0.15) \times (m_{total})$] has been recorded on the strain gauge. The sample is then removed from the NaCl solution, but is kept in a vertical configuration.

The sample is then subjected to test methods to determine the fluid distribution profile of the sample. Any test method may be used to determine the fluid distribution profile of the sample. One known method is to cut the absorbent composite into strips having a width of ½ inch (1.27 cm), and weighing the strips to determine the amount of fluid within a given strip. In the above sample, twenty strips having a width of ½ inch (1.27 cm) and a length of 3.5 inch (8.89 cm) are produced from each composite sample. A fluid distribution profile is determined by weighing each strip to determine the amount of fluid in each strip. The fluid amount is determined for each strip by the following equation: Fluid amount per strip=wet weight of strip–(dry weight of full sample/20).

The IVW procedure is repeated with two more composite samples cut from the same composite material. An average pickup time is determined for the three first liquid pickups, the three second liquid pickups, and the three third liquid pickups. Further, the average amount of liquid in each ½ inch segment of the three composite sample is determined as described above.

Fluid Intake Evaluation (FIE) Test

The Fluid Intake Evaluation (FIE) test measures the intake capability of a material or composite. The test consists of subjecting an absorbent composite to three liquid insults, wherein each liquid insult represents 30% of the saturated capacity of the composite as determined by the SC test described above. The three liquid insults are spaced apart at 15 minute intervals.

A composite of superabsorbent and fluff is air-formed on tissue to a desired basis weight and density. A composite sample is cut to a desired size, in this case, the composite sample is cut to a 3.5 inch (8.89 cm) by 5 inch (12.70 cm) rectangle. The saturation capacity of the sample ($m_{total}$) is determined as described above. An amount equal to $(0.30) \times (m_{total})$ is calculated.

Figure 2:
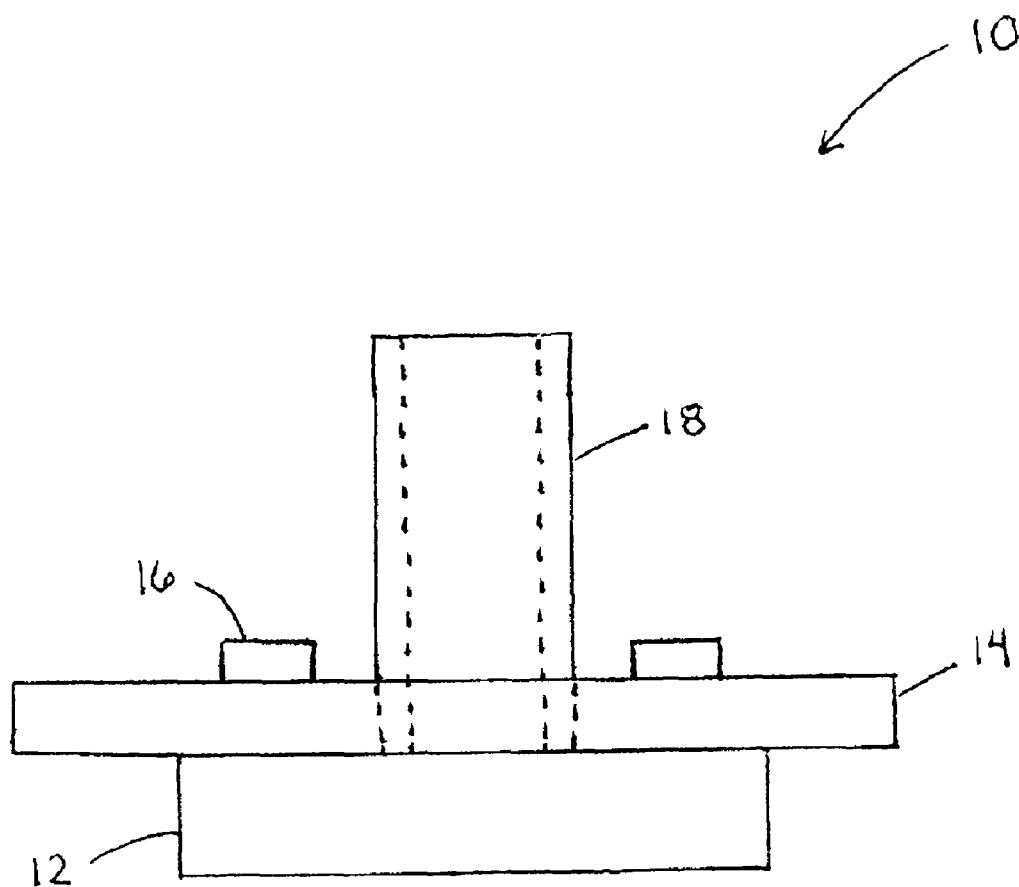
FIG. 2 is a perspective view of a liquid addition device.

A liquid addition device 10, as shown in FIG. 2, is placed on the top of a separate composite sample 12 (also cut to a 3.5 inch (8.89 cm) by 5 inch (12.70 cm) rectangle) to produce a pressure of approximately 0.13 psi (8966 dynes/$cm^2$). The liquid addition device includes a base 14 and additional brass weight 16 to make the total mass of the device 10 equal to 1223 grams. Liquid is brought into contact with the sample 12 by introducing the liquid through a tube 18 located on the liquid addition device 10. A first liquid insult of a 0.9 wt % NaCl solution, equal to 30% of the saturation capacity of the absorbent composite [$(0.30) \times (m_{total})$], is introduced through the tube 18 and brought into contact with the composite sample 12. The amount of time required for all of the first liquid insult to be soaked into the composite sample 12 is measured. After 15 minutes from the beginning of the first insult, a second liquid insult of the 0.9 wt % NaCl solution, equal to 30% of the saturation capacity of the absorbent composite [$(0.30) \times (m_{total})$], is brought into contact with the composite sample 12. The amount of time required for all of the second liquid insult to be soaked into the composite sample 12 is measured. After an additional 15 minutes from the beginning of the second insult, a third liquid insult of the 0.9 wt % NaCl solution, equal to 30% of the saturation capacity of the absorbent composite [$(0.30) \times (m_{total})$], is brought into contact with the composite sample 12. The amount of time required for all of the third liquid insult to be soaked into the composite sample 12 is measured.

The procedure is repeated with two more composite samples cut from the same composite material. An average intake time is calculated for the three first, for the three second, and for the three third liquid insults. Additionally, a total insult average intake time is calculated as the sum of the first, second, and third insult average intake times.

Those skilled in the art will readily understand that the superabsorbent materials and absorbent composites of the present invention may be advantageously employed in the preparation of a wide variety of products, including but not limited to, absorbent personal care products designed to be contacted with body fluids. Such products may only comprise a single layer of the absorbent composite or may comprise a combination of elements as described above. Although the superabsorbent materials and absorbent composites of the present invention are particularly suited for personal care products, the superabsorbent materials and absorbent composites may be advantageously employed in a wide variety of consumer products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

In the Examples below, absorbent composites were produced using the following superabsorbent materials and fibrous materials:

Superabsorbent Material

AFA-177-9A, AFA-177-9B, AFA-177-140 and Drytech 2035, supplied by Dow Chemical Co. of Midland, Mich.

Fibrous Material

Fluffed pulp fibers, CR-1654, supplied by Alliance Forest Products of Coosa Pines, Ala.

Example 1

Determining the Particle Size Distribution of Superabsorbent Material Samples

Two 100 g samples of AFA-177-9A and AFA-177-9B were supplied by Dow Chemical Co. of Midland, Mich. The particle size distribution of each sample was measured using the above-described PSD Test Method. Sieves having the following mesh sizes were used for Sample AFA-177-9A: 1680 microns, 1190 microns, 1000 microns, and 850 microns. Sieves having the following mesh sizes were used for Sample AFA-177-9B: 150 microns, 105 microns, and 63 microns.

The particle size distributions of Samples AFA-177-9A and AFA-177-9B are given below in Tables 1 and 2.

TABLE 1

Particle Size Distributions of Sample AFA-177-9A.

| Particle Size (microns) | Mass % of Total |
|---|---|
| greater than 1680 | 0.02 |
| 1190–1680 | 31.2 |
| 1000–1190 | 27.25 |
| 850–1000 | 36.51 |
| less than 850 | 5.03 |

TABLE 2

Particle Size Distributions of Sample AFA-177-9B.

| Particle Size (microns) | Mass % of total |
|---|---|
| greater than 150 | 1.74 |
| 105–150 | 45.05 |
| 63–105 | 48.97 |
| less than 63 | 4.23 |

As can be seen from Tables 1 and 2 above, the mass median particle size of the particles in Samples AFA-177-9A and AFA-177-9B are about 1100 microns and 100 microns respectively.

Example 2

Preparation of Absorbent Composites of the Present Invention

Absorbent composites were formed using superabsorbent material AFA-177-140 supplied by Dow Chemical Co. of Midland, Mich. and pulp fibers, CR-1654, supplied by Alliance Forest Products of Coosa Pines, Ala. Superabsorbent material AFA-177-140 had essentially the same chemical composition as samples AFA-177-9A and AFA-177-9B of Example 1. The AFA-177-140 superabsorbent material was ground using methods known in the art to yield two samples, Sample 1A and Sample 1B, having particle size distributions similar to Samples AFA-177-9A and AFA-177-9B described in Example 1. The composites were formed via a conventional air-forming unit. The mass ratio of Sample 1A (large particles) to Sample 1B (small particles) in the composites was varied as follows: 50:50, 70:30, 80:20, and 90:10. The composites had a target total basis weight of 500 gsm, a target density of 0.2 g/cc, and a SAP concentration of 50% by mass.

The mass median particle size of the particles in Samples 1A and 1B at a saturation level of 30 gm of 0.9 wt. % of NaCl solution per gm of SAP. was determined. Further, the void spaces in the saturated superabsorbent particle beds and the specific gravity of the particles were determined experimentally using the Gel Bed Void Space Experimental Procedure. The results are given in Table 3 below.

TABLE 3

Parameters For Theoretical Particle Ratio Calculation.

| | Mass Medium Dry Diameter (microns) | Mass Medium Saturated Diameter (microns) | Voids @30g/g (v) | Specific Gravity (ρ) |
|---|---|---|---|---|
| Component 1 | 1100 | 3930 | 0.18 | 1.02 |
| Component 2 | 105 | 375 | 0.07 | 1.02 |

Using the equations above along with the values for $v_1$ (the void space in a system of Sample 1A particles), $v_2$ (the void space in a system of Sample 1B particles), $\rho_1$ (the true specific gravity of Sample 1A particles), and $\rho_2$ (the true specific gravity of Sample 1B particles), determined experimentally, the theoretical optimum large particle (Sample 1A particles) to small particle (Sample 1B particles) ratio was determined as shown below.

$$\varphi_1 = [(1-v_1)\cdot\rho_1] \div [(1-v_1)\cdot\rho_1 + v_1\cdot(1-v_2)\cdot\rho_2]$$

$$= [(1-0.18)\cdot 1.02] \div [(1-0.18)\cdot 1.02 + 0.18\cdot(1-0.07)\cdot 1.02]$$

$$= 0.83$$

$$\Phi = \varphi_1 + (1-\varphi_1)$$

$$= 0.83 + (1-0.83)$$

$$= 1$$

The theoretical weight percent of each component should be:

$\phi_1/\Phi$=weight % of component:

Wt % of Sample 1A (large particles)=$(\phi_1/\Phi)\times 100=83\%$

Wt % of Sample 1B (small particles)=$[(1-\phi_1)/\Phi]\times 100=17\%$

Since both components are assumed to be at the same saturation level at equilibrium, the dry weight percentages will be the same as the saturated weight percentages calculated above.

Example 3

Preparation of Control Absorbent Composites Using a Conventional Particle Size Distribution A control absorbent composite was made using the same materials as in Example 2, except that the superabsorbent material had a particle size distribution ranging from 0 to 850 microns. This control is referred to herein as Control 1. Specifically, Control 1 was determined to have a particle size distribution as shown below.

TABLE 4

Mass Median Particle Size Distribution of Control 1

| Particle size (microns) | Weight % of total |
|---|---|
| 600–850 | 25 |
| 300–600 | 50 |
| 65–300 | 25 |

A second control composite was prepared using 50% Drytech 2035 supplied by Dow Chemical Co. of Midland, Mich. and 50% Alliance CR-1654 fluff supplied by Alliance Forest Products of Coosa Pines, Ala. This composite was formed in order to compare the composites of the present invention with a composite comprising a representative superabsorbent material that is used in commercial products.

The control composite containing the Drytech 2035 is hereinafter referred to as Control 2. Table 5 sets forth the particle size distribution of Control 2.

TABLE 5

Mass Median Particle Size Distribution of Control 2

| Particle size (microns) | Weight % of total |
|---|---|
| 600–850 | 20 |
| 300–600 | 55 |
| 65–300 | 25 |

Example 4

Wicking Performance of Absorbent Composites of the Present Invention and Control Composites The wicking performance of the composites of Examples 2 and 3 were assessed using the Intermittent Vertical Wicking (IVW) test described above. The fluid distribution within each composite was analyzed after the third liquid insult by determining the liquid amount in each 0.5 inch segment of the composite. The liquid amount in each section was divided by the liquid amount for that sample in the 0–0.5 inch segment for that sample. This value was multiplied by 100 to obtain the percentages displayed below in Table 6.

TABLE 6

Average Fluid Distribution After $3^{rd}$ Insult

| Distance From Lower Edge | Absorbent Composite Average Fluid Distribution After $3^{rd}$ Insult (% of lowest segment saturation level) | | | | | |
|---|---|---|---|---|---|---|
| (inches) | 50:50 | 70:30 | 80:20 | 90:10 | Control 1 | Control 2 |
| 0–0.5 | 100% | 100% | 100% | 100% | 100% | 100% |
| 0.5–1.0 | 110% | 102% | 103% | 95% | 101% | 98% |
| 1.0–1.5 | 98% | 97% | 94% | 92% | 94% | 93% |
| 1.5–2.0 | 89% | 91% | 92% | 78% | 95% | 83% |
| 2.0–2.5 | 83% | 83% | 83% | 81% | 84% | 77% |
| 2.5–3.0 | 78% | 79% | 74% | 68% | 63% | 71% |
| 3.0–3.5 | 68% | 69% | 70% | 69% | 49% | 62% |
| 3.5–4.0 | 65% | 61% | 54% | 59% | 44% | 57% |
| 4.0–4.5 | 58% | 50% | 42% | 47% | 26% | 45% |
| 4.5–5.0 | 47% | 39% | 28% | 32% | 14% | 33% |
| 5.0–5.5 | 32% | 28% | 10% | 25% | 4% | 12% |
| 5.5–6.0 | 15% | 13% | 5% | 10% | 4% | 1% |
| 6.0–6.5 | 4% | 5% | 5% | 5% | 4% | 0% |
| 6.5–7.0 | 3% | 4% | 4% | 5% | 3% | 0% |

As can be seen from the data in Table 6, better fluid distribution and wicking was experienced with the composites containing a bimodal superabsorbent particle size distribution. This is evident by the larger amounts of fluid located in the higher portions of the composites (>5").

The fluid distribution of the absorbent composites of the present invention was enhanced by the presence of a bimodal particle size distribution as seen by the increased amount of fluid in the higher portions of the composites. The rate of fluid pickup during the IVW test was also found to be enhanced in some of the bimodal systems as shown in Tables 7 and 8 below.

TABLE 7

Average $3^{rd}$ Insult Pickup Versus Time

| Time Interval | Absorbent Composite Average $3^{rd}$ Insult Pickup Amount at Given Time (g) | | | | | |
|---|---|---|---|---|---|---|
| (seconds) | 50:50 | 70:30 | 80:20 | 90:10 | Control 1 | Control 2 |
| 50 | 8.5 | 10.5 | 15.5 | 10.5 | 11.0 | 12.3 |
| 100 | 12.0 | 15.5 | 18.5 | 12.5 | 14.1 | 15.0 |
| 150 | 14.0 | 17.5 | 22.0 | 15.0 | 17.0 | 18.0 |
| 200 | 16.0 | 20.5 | 24.5 | 16.5 | 17.7 | 19.6 |
| 250 | 16.5 | 22.5 | 25.0 | 17.5 | 18.9 | 20.5 |
| 300 | 17.0 | 23.0 |  | 18.5 | 20.5 | 19.5 |
| 350 | 19.5 | 23.5 |  | 20.0 | 21.7 | 20.9 |
| 400 | 21.0 | 24.0 |  | 21.5 | 22.7 | 22.1 |
| 450 | 21.5 | 24.5 |  | 22.0 | 24.2 | 23.1 |
| 500 | 21.8 | 25.0 |  | 23.0 | 24.8 | 23.9 |
| Target Pickup Amount (gm) | 25.0 | 25.0 | 25.0 | 25.0 | 25.0 | 31.0 |

TABLE 8

Average $3^{rd}$ Insult Pickup

| Time Interval | Absorbent Composite Average $3^{rd}$ Insult Pickup Amount Expressed As Percentage of Target Pickup Amounts | | | | | |
|---|---|---|---|---|---|---|
| (seconds) | 50:50 | 70:30 | 80:20 | 90:10 | Control 1 | Control 2 |
| 50 | 34% | 42% | 62% | 42% | 44% | 40% |
| 100 | 48% | 62% | 74% | 50% | 56% | 48% |
| 150 | 56% | 70% | 88% | 60% | 68% | 58% |
| 200 | 64% | 82% | 98% | 66% | 71% | 63% |
| 250 | 66% | 90% | 100% | 70% | 76% | 66% |
| 300 | 68% | 92% |  | 74% | 82% | 63% |
| 350 | 78% | 94% |  | 80% | 87% | 67% |
| 400 | 84% | 96% |  | 86% | 91% | 71% |
| 450 | 86% | 98% |  | 88% | 97% | 75% |
| 500 | 87% | 100% |  | 92% | 99% | 77% |

As can be seen from the data in Table 7 and Table 8, wicking rates were affected by the amount of large and small particles present in the absorbent composite. The average $3^{rd}$ insult fluid pick up suggests that the presence of too many small particles or large particles negatively impacts the wicking rate of the composite. It is believed that the tendency of small particles to cause gel blocking and the reduced capillarity caused by the large particles negatively impacts the wicking rate of the composite.

Further, it should be noted that the wicking rate of an absorbent composite having a bimodal particle distribution and a 80:20 wt/wt ratio showed improvement over the control composites having a regular particle distribution.

The above data from Tables 6–8 suggests that the fluid distribution and wicking rate can be improved in composites containing the proper large particle to small particle ratio in a bimodal superabsorbent particle size distribution.

Example 5

Fluid Intake Performance of Absorbent Composites of the Present Invention and Control Composites The intake performance of the composites of Example 2 and the Control composites of Example 3 were evaluated using the Fluid Intake Evaluation (FIE) as described in the "Test Method" section above. The FIE results are given below in Table 9.

TABLE 9

FIE Results For Absorbent Composites

| Sample | Weight Ratio of Sample 1A to Sample 1B | First Insult Average Intake Time (sec) | Second Insult Average Intake Time (sec) | Third Insult Average Intake Time (sec) | Total Insult Average Intake Time (sec) |
|---|---|---|---|---|---|
| Ex. 2 | 50:50 | 71.2 | 73.2 | 96.2 | 240.6 |
| Ex. 2 | 70:30 | 38.7 | 38.6 | 63.6 | 140.9 |
| Ex. 2 | 80:20 | 45.2 | 29.5 | 46.8 | 121.5 |
| Ex. 2 | 90:10 | 61.6 | 38.9 | 80.8 | 181.3 |
| Control 1 | n/a | 46.6 | 101.2 | 170.2 | 318.0 |
| Control 2 | n/a | 41.6 | 55.7 | 108 | 205.3 |

As seen from the data in Table 9, composite samples having a superabsorbent material weight ratio of 80 wt % of Sample 1A (large particles) to 20 wt % of Sample 1B (small particles) yielded the lowest total insult average intake time, as well as, the lowest average second and third insult intake time.

Example 6

Swelling Time Determination of Superabsorbent Particles in Absorbent Composites of the Present Invention The swelling time of the large particles of Sample AFA-177-9A and the small particles of Sample AFA-177-9B was determined using the Blotted FAUZL test as described above. The results of the test are provided in Table 10 below.

TABLE 10

Swelling Time of Superabsorbent Particles

| Particle Size | Time to reach 60% saturation (in seconds) |
|---|---|
| Sample AFA-177-9A (large particles) | 578 |
| Sample AFA-177-9B (small particles) | 28.3 |

The above disclosed examples are preferred embodiments and are not intended to limit the scope of the present invention in any way. Various modifications and other embodiments and uses of the disclosed superabsorbent polymers, apparent to those of ordinary skill in the art, are also considered to be within the scope of the present invention.

What is claimed is:

1. An absorbent composite comprising superabsorbent material, wherein the superabsorbent material comprises a blend of superabsorbent particles having a bimodal particle size distribution with large particles having a mass median particle size from about 850 to about 1800 microns and small particles having a mass median particle size from about 50 to about 200 microns and the superabsorbent particles have an overall mass median particle size of about 60 to about 1750 microns.

2. The absorbent composite of claim 1, wherein the large particles have a mass median particle size from about 1000 to about 1600 microns.

3. The absorbent composite of claim 1, wherein the small particles have a mass median particle size from about 65 to about 150 microns.

4. The absorbent composite of claim 1, wherein the superabsorbent particles have an overall mass median particle size of about 800 to about 1200 microns.

5. The absorbent composite of claim 1, wherein the mass median particle size of the large particles and the mass median particle size of the small particles differs by at least about 500 microns.

6. The absorbent composite of claim 5, wherein the ratio of the mass median particle size of the large particles to the mass median particle size of the small particles is from about 4:1 to about 36:1.

7. The absorbent composite of claim 6, wherein the ratio of the mass median particle size of the large particles to the mass median particle size of the small particles is from about 6:1 to about 25:1.

8. The absorbent composite of claim 5, wherein the mass median particle size of the large particles is from about 1000 to about 1200 microns, and the mass median particle size of the small particles is from about 50 to about 150 microns.

9. The absorbent composite of claim 8, wherein the mass median particle size of the large particles is from about 1000 to about 1100 microns, and the mass median particle size of the small particles is from about 50 to about 100 microns.

10. The absorbent composite of claim 1, wherein the mass ratio of large particles to small particles is from about 90:10 to about 50:50.

11. The absorbent composite of claim 10, wherein the mass ratio of large particles to small particles is from about 90:10 to about 80:20.

12. The absorbent composite of claim 11, wherein the mass ratio of large particles to small particles is about 85:15.

13. The absorbent composite of claim 1, wherein the superabsorbent material is uniformly distributed within the composite.

14. The absorbent composite of claim 1, wherein the absorbent composite comprises from about 20% to about 100% by weight superabsorbent material.

15. The absorbent composite of claim 14, wherein the absorbent composite comprises from about 30% to about 90% by weight superabsorbent material.

16. The absorbent composite of claim 1, further comprising a containment device.

17. The absorbent composite of claim 16, wherein the containment device is a fibrous matrix.

18. The absorbent composite of claim 1, wherein the absorbent composite has a third liquid insult intake time less than about 100 seconds.

19. The absorbent composite of claim 18, wherein the absorbent composite has a third liquid insult intake time less than about 85 seconds.

20. The absorbent composite of claim 19, wherein the absorbent composite has a third liquid insult intake time less than about 60 seconds.

21. The absorbent composite of claim 1, wherein the absorbent composite has a third intermittent vertical wicking pickup time less than about 600 seconds.

22. The absorbent composite of claim 21, wherein the absorbent composite has a third intermittent vertical wicking pickup time less than about 300 seconds.

23. The absorbent composite of claim 1, wherein the small particles have a swelling time from about 15 to about 35 seconds and the large particles have a swelling time from about 300 to about 700 seconds.

24. The absorbent composite of claim 23, wherein the swelling time of the small particles is about 20 times shorter than the swelling time of the large particles.

25. An absorbent composite comprising superabsorbent material, wherein the superabsorbent material comprises a blend of superabsorbent particles having a bimodal particle size distribution, and wherein the absorbent composite has a third liquid insult intake time less than about 100 seconds.

26. The absorbent composite of claim 25, wherein the absorbent composite has a third liquid insult intake time less than about 85 seconds.

27. The absorbent composite of claim 26, wherein the absorbent composite has a third liquid insult intake time less than about 60 seconds.

28. The absorbent composite of claim 25, wherein the absorbent composite has a third intermittent vertical wicking pickup time less than about 600 seconds.

29. The absorbent composite of claim 28, wherein the absorbent composite has a third intermittent vertical wicking pickup time less than about 300 seconds.

30. The absorbent composite of claim 25, wherein the superabsorbent material is uniformly distributed within the composite.

31. The absorbent composite of claim 25, wherein the superabsorbent particles comprise small particles having a swelling time from about 15 to about 35 seconds and large particles having a swelling time from about 300 to about 700 seconds.

32. The absorbent composite of claim 31, wherein the swelling time of the small particles is about 20 times shorter than the swelling time of the large particles.

33. The absorbent composite of claim 25, wherein the superabsorbent particles comprise large particles having a mass median particle size from about 850 to about 1800 microns.

34. The absorbent composite of claim 25, wherein the superabsorbent particles comprise small particles having a mass median particle size from about 50 to about 200 microns.

35. The absorbent composite of claim 25, wherein the absorbent composite comprises from about 30% to about 90% by weight superabsorbent material.

36. The absorbent composite of claim 25, wherein the mass ratio of large particles to small particles is from about 90:10 to about 50:50.

37. An absorbent composite comprising superabsorbent material, wherein the superabsorbent material is uniformly distributed within the composite, and wherein the composite has a third liquid insult intake time less than about 100 seconds and a third intermittent vertical wicking pickup time of less than about 600 seconds.

38. The absorbent composite of claim 37, wherein the composite has a third liquid insult intake time less than about 85 seconds.

39. The absorbent composite of claim 38, wherein the composite has a third liquid insult intake time less than about 60 seconds.

40. The absorbent composite of claim 37, wherein the composite has a third intermittent vertical wicking pickup time of less than about 300 seconds.

41. The absorbent composite of claim 37, wherein the composite comprises from about 20% to about 100% by weight superabsorbent material.

42. The absorbent composite of claim 41, wherein the composite comprises from about 30% to about 90% by weight superabsorbent material.

43. The absorbent composite of claim 37, further comprising a containment device.

44. The absorbent composite of claim 1, wherein the mass ratio of large particles to small particles is from about 70:30 to 90:10.

45. The absorbent composite of claim 25, wherein the mass ratio of large particles to small particles is from about 70:30 to 90:10.

46. The absorbent composite of claim 37, wherein the mass ratio of large particles to small particles is from about 70:30 to 90:10.

47. An absorbent product comprising the absorbent composite of claim 1.

48. An absorbent product comprising the absorbent composite of claim 25.

49. An absorbent product comprising the absorbent composite of claim 37.

50. An absorbent product of claim 47, wherein the product is a diaper, training pant, catamenial device, incontinence product, bed pad, wound dressing, delivery system, wipe, bib or food packaging.

51. An absorbent product of claim 48, wherein the product is a diaper, training pant, catamenial device, incontinence product, bed pad, wound dressing, delivery system, wipe, bib or food packaging.

52. An absorbent product of claim 49, wherein the product is a diaper, training pant, catamenial device, incontinence product, bed pad, wound dressing, delivery system, wipe, bib or food packaging.

53. An absorbent product of claim 47, further comprising a topsheet and a backsheet, wherein the absorbent composite is positioned between the topsheet and the backsheet.

54. An absorbent product of claim 48, further comprising a topsheet and a backsheet, wherein the absorbent composite is positioned between the topsheet and the backsheet.

55. An absorbent product of claim 49, further comprising a topsheet and a backsheet, wherein the absorbent composite is positioned between the topsheet and the backsheet.

* * * * *